United States Patent
Fromm et al.

(10) Patent No.: US 6,946,586 B1
(45) Date of Patent: Sep. 20, 2005

(54) GENETIC TRAIT BREEDING METHOD

(75) Inventors: Michael Fromm, Kensington, CA (US); James Zhang, Palo Alto, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 09/958,131

(22) PCT Filed: Apr. 6, 2000

(86) PCT No.: PCT/US00/09448

§ 371 (c)(1),
(2), (4) Date: Jan. 30, 2002

(87) PCT Pub. No.: WO00/60089

PCT Pub. Date: Oct. 12, 2000

Related U.S. Application Data

(63) Continuation-in-part of application No. 09/837,944, filed on Apr. 18, 2001, now abandoned, and a continuation-in-part of application No. 09/713,994, filed on Nov. 16, 2000.
(60) Provisional application No. 60/128,153, filed on Apr. 7, 1999.

(51) Int. Cl.$^7$ .................. C12N 15/82; C12N 15/90; A01H 1/00; A01H 5/00
(52) U.S. Cl. ........................ 800/278; 435/468
(58) Field of Search ............... 435/320.1, 419, 435/468; 800/260, 278, 289

(56) References Cited

U.S. PATENT DOCUMENTS 5,968,793 A * 10/1999 Liu et al. .............. 435/468

OTHER PUBLICATIONS

Kasuga et al., Nature Biotech., Mar. 1999, vol. 17, pp. 287–291.*
Tang et al., Plant Cell, Jan. 1999, vol. 11, pp. 15–29.*
Chung et al., Plant Mol. Biol., 1994, vol. 26, pp. 657–665.*
Moore et al., Proc. Natl. Acad. Sci. USA, Jan. 1998, vol. 95, pp. 376–381.*

* cited by examiner

*Primary Examiner*—Ashwin Mehta
(74) *Attorney, Agent, or Firm*—Jeffrey M. Libby; Matthew R Kaser

(57) ABSTRACT

A method for screening for a trait associated with the altered expression of a gene of interest in plants is provided. The method is a combinatorial approach which uses traditional plant breeding techniques for modifying the patterns of expression of a gene of interest. Kits for use in the method and transgenic plants generated by the method are also provided.

22 Claims, 1 Drawing Sheet

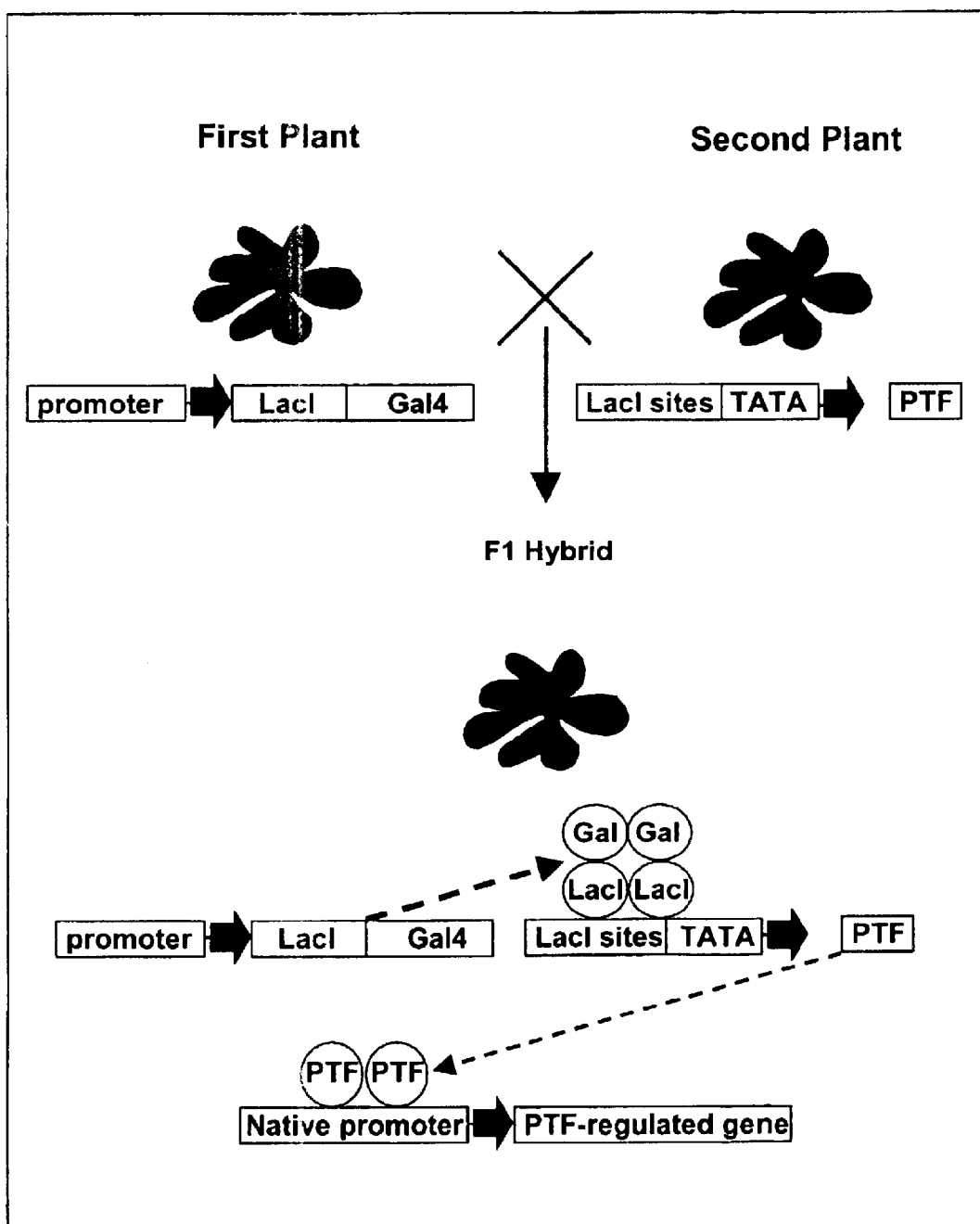

GENETIC TRAIT BREEDING METHOD

This patent application is a continuation-in-part of the following and commonly assigned applications: U.S. non-provisional application Ser. No. 09/713,994, filed Nov. 16, 2000, and U.S. non-provisional application Ser. No. 09/837,944, filed Apr. 18, 2001, now abandoned, and is also the national stage of PCT/US00/09448, filed Apr. 6, 2000, which claims the benefit of U.S. Provisional Application Ser. No. 60/128,153, filed Apr. 7, 1999.

FIELD OF THE INVENTION

This invention is in the field of plant molecular biology. In particular, this invention relates to a method for breeding plants for improved agricultural traits.

BACKGROUND OF THE INVENTION

To date, almost all improvements in agricultural crops have been achieved using traditional plant breeding techniques. These techniques involve crossing parental plants with different genetic backgrounds to generate progeny with genetic diversity. The progeny are then selected to obtain those plants that express the desired traits. Desired traits are then fixed while deleterious traits are eliminated via multiple backcrossings or selfings to eventually yield progeny with the desired characteristics. Hybrid corn, low erucic acid oilseed rape, high oil corn, and hard white winter wheat are examples of significant agricultural advances achieved with traditional breeding.

However, the amount of genetic diversity in the germplasm of a particular crop limits what can be accomplished by breeding. Although traditional breeding has proven to be very powerful, as advances in crop yields over the last century demonstrate, recent data suggest that the rate of yield improvement is tapering off for major food crops (Lee (1998) *Proc. Natl. Acad. Sci. USA* 95: 2001–2004). The introduction of molecular mapping markers into breeding programs may accelerate the process of crop improvement in the near term, but ultimately the lack of new sources of genetic diversity will become limiting. In particular, traditional breeding has proved rather ineffective for improving many polygenic traits such as increased disease resistance.

In recent years, biotechnology approaches involving the expression of single transgene in crops have resulted in the successful commercial introduction of new plant traits, including herbicide resistance (glyphosate or Roundup resistance), insect resistance (expression of *Bacillus thuringiensis* toxins) and virus resistance (over expression of viral coat proteins). However, the list of single gene traits of significant value is relatively small. The greatest potential of biotechnology lies in engineering complex polygenic traits for environmental stresses, disease, plant development and architecture, yield and quality traits. Presently, engineering such polygenic traits has proven extremely challenging.

The present invention provides a novel method for the rapid identification of genes that are useful for modifying complex plant traits.

BRIEF DESCRIPTION OF THE DRAWING

The FIGURE in the instant application depicts a cross between a plant transformed with a donor vector (an activator plant) and a plant transformed with a receptor vector containing a promoter linked to a transactivator gene. In this FIGURE the promoter and transactivator gene are a fusion of the Lac I binding domain and the Gal4 transactivation domain. Only after activator and target plants are crossed is the plant transcription factor over-or-underexpressed by having the transactivator bind to its binding site on the plant transcription factor gene construct.

SUMMARY OF THE INVENTION

In one aspect, the invention provides a systematic method for screening for traits associated with the altered expression of a gene of interest in plants. The method comprises providing a first pool of donor vectors, wherein each donor vector comprises a transactivator and a second pool of receptor vectors, wherein each receptor vector comprises a transactivator binding site operably linked to a different gene of interest. Then a first plant is transformed with a member of the donor vector pool and a second plant transformed with a member of the receptor vector pool to generate first transformed plants comprising the donor vector and a second transformed plant comprising the receptor vector. First and second transformed plants are crossed to generate a hybrid plant. Both first and second transformed plants have a wild type phenotype because the expression levels of the gene of interest is not altered from that in a nontransformed plant. However, the phenotype of the hybrid plant comprising both transactivator and the gene of interest may be different from wild type because the expression levels of the gene of interest is altered compared with that of a nontransformed plant. The phenotype of these plants is investigated to identify a hybrid plant with an improved trait.

The transactivator may be operably linked to (1) a constitutive promoter, (2) an inducible promoter, (3) a tissue active or specific promoter or (4) a developmental-stage active or specific promoter. When the transactivator is linked to a constitutive promoter, changes in expression of a gene will be observed in all tissues and at all times and a broad overview of the effects of the expression of the gene on a plant will be observed. When the transactivator is linked to a tissue specific promoter or an inducible promoter or developmental-stage promoter, the expression of the gene may be turned on or off in a particular tissue such as seed, roots, flowers, leaves, shoots, fruits or stems, during a particular period in development, such as early, middle or late stages in development, or under particular conditions, such as specific environmental or disease stresses. A plant may be transformed with more than one receptor vector or with more than one donor vector.

The gene of interest may be any gene, but is preferably a regulatory gene such as a transcription factor, a phosphatase or a protein kinase. In one preferred embodiment, the genes of interest are all the transcription factors identified in a plant, such as those identified in *Arabidopsis thaliana*. These genes collectively control all gene expression in plants and thus control all plant traits. The gene may be in a sense orientation for overexpression analysis or in an antisense orientation for underexpression analysis. Additionally, the gene may be a full length coding sequence for a gene or a fragment of a gene, in particular a fragment with biological activity.

The donor and receptor vectors may also include first and second selectable markers, respectively, to assist in selecting transformed hybrid plants.

In a second aspect, the invention provides a method for breeding plants for a desired or improved trait. The method involves crossing a member of a first pool of plants, each plant in this pool having been transformed with an donor vector comprising a transactivator, with a member of a second pool of plants, each plant in this pool having been transformed with a receptor vector comprising a transactivator binding site operably linked to a different gene of interest to generate a collection of hybrid plants. Traditional plant breeding techniques are used to obtain transgenic plants having both donor and receptor vectors and exhibiting a desired or improved trait. Additionally, the invention provides a transgenic plant generated by the method described above.

In yet another aspect, the invention is a plant breeding kit. The plant breeding kit comprises (a) a pool of activator vectors, wherein each donor vector comprises a transactivator; and (b) a pool of receptor vectors, wherein each receptor vector comprises a transactivator binding site operably linked to a different gene of interest. The vectors may also include first and second selectable markers to assist in selecting transformed hybrid plants. The transactivator may be operably linked to (1) a constitutive promoter, (2) an inducible promoter, (3) a tissue active or specific promoter or (4) a developmental-stage active or specific promoter.

Individual donor vectors and receptor vectors are transformed into first and second plants, respectively, and traditional plant breeding techniques are employed to generate hybrid plants comprising first and second vectors with agriculturally valuable traits.

In a further aspect, the invention is a method for modifying the patterns of gene expression in a plant. The method first entails providing a first pool of donor vectors, wherein each activator vector member comprises a transactivator, and a second pool of receptor vectors, wherein each receptor vector member comprises a transactivator binding site operably linked to a regulatory gene. Activator and receptor vector members are transformed into first and second plants. Transformed first and second plants are crossed to generate a hybrid plant with modified patterns of gene expression.

DETAILED DESCRIPTION OF THE INVENTION

Definitions

A "transgenic or transformed plant" refers to a plant which contains a recombinant polynucleotide introduced by transformation. Transformation means introducing a nucleotide sequence in a plant in any manner to cause stable or transient expression of the sequence. This may be achieved by transfection with viral vectors, transformation with plasmids, such as *Agrobacterium*-based vectors, or introduction of naked DNA by electroporation, lipofection, or particle gun acceleration. A transformed plant; may refer to a whole plant as well as to seed, plant tissue, plant cells or any other plant material, and to the plant's progeny.

A "vector" is a nucleic acid construct, generated recombinantly or synthetically, comprising nucleic acid elements that can cause expression of a gene. A "donor vector" is a construct for expression of a polynucleotide sequence for a transactivator gene. The transactivator gene is operably linked to a promoter. The promoter region may include tissue active-or-specific promoters, developmental stage active-or-specific promoters, inducible promoters or constitutive promoters.

A "receptor vector" is a construct for expression of a gene of interest such as regulatory gene. Typically, the receptor vector includes the sequence for a transactivator binding site. The construct sequence may also include promoters, operators, enhancer regions, silencer regions, polyadenylation sites, translation initiation sites and the like.

A "gene of interest" is a polynucleotide sequence for a regulatory gene such as a transcription factor, a protein kinase or a phosphatase. These sequences may be in a sense or antisense orientation, or partial or complete gene sequences.

A nucleotide sequence is "operably linked" when it is placed into a functional relationship with another nucleotide sequence. For example, a promoter or enhancer is operably linked to a gene coding sequence if the presence of the promoter or enhancer increases the level of expression of the gene coding sequence.

A "pool" entails a group of at least two members, preferably at least 10 members, more preferably at least 100 members. For example, a pool can be all the identified genes of a certain type in a plant such as all identified transcription factors derived from a plant, as exemplified by up to 1,700 transcription factors identified in *Arabidopsis thaliana*.

The phrase "altered or modified expression" in reference to polynucleotide or polypeptide expression refers to an expression pattern in a transgenic plant that is different from the expression pattern in the wild type plant or a reference plant; for example, by expression in a cell type other than a cell type in which the sequence is expressed in the wild type plant, or by expression at a time other than at the time the sequence is expressed in the wild type plant, or by a response to different inducible agents, such as hormones or environmental signals, or at different expression levels (either higher or lower) compared with those found in a wild type plant. The term also refers to lowering the levels of expression to below the detection level or completely abolishing expression. The resulting expression pattern may be transient or stable, constitutive or inducible.

"Trait" refers to the physiological, morphological or physical characteristics of a plant or particular plant material. These characteristics may be visible to the human eye, such as germination rates or seed size, or be measurable by laboratory techniques, such as the protein, starch or oil content of seed by biochemical assays or changes in the expression level of genes by employing Northerns, RT PCR or microarray gene expression assays.

Trait modifications or improvements of particular interest include those to seed, fruit, root, flower, leaf, stem, shoot, seedling or the like, including: enhanced tolerance to environmental conditions including freezing, chilling, heat, drought, water saturation, radiation and ozone; enhanced resistance to microbial, fungal or viral diseases; resistance to nematodes, decreased herbicide sensitivity, enhanced tolerance of heavy metals (or enhanced ability to take up heavy metals), enhanced growth under poor photoconditions (e.g., low light and/or short day length), or changes in expression levels of genes of interest. Other traits that may modified relate to the production of plant metabolites, such as variations in the production of taxol, tocopherol, tocotrienol, sterols, phytosterols, vitamins, wax monomers, antioxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that may be modified include cell development, fruit and seed size and number, yields of plant parts such as stems, leaves and roots, the stability of the seeds during storage, characteristics of the seed pod (e.g., susceptibility to shattering), root hair length and quantity, internode distances, or the quality of seed coat. Plant growth characteristics that may be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ Identity, organ shape or size.

"Hybrid plant" refers to a plant generated by crossing two plants of interest, propagating by seed or tissue and then growing the plants. When plants are crossed sexually, the step of pollination may include cross pollination or self pollination or back crossing with an untransformed plant or another transformed plant. Hybrid plants include first generation and later generation plants.

The present invention provides a method to manipulate and improve a plant trait. The method combines the power of genomics with plant breeding techniques. In the method, the expression levels of known genes of interest in a plant can be altered constitutively, or altered selectively to monitor tissue specific expression, inducible expression, developmental-stage specific expression or the like in a high-throughput manner. Phenotypic changes resulting from expressing specific plant genes at different levels, at different times, under different types of stress, in different plant tissues or the like is then screened. Finally, plants with improved traits are selected.

The method entails transforming a first plant with a member of a first pool of donor vectors. Each donor vector includes a transactivator that is placed under the control of a different promoter so that the expression of the transactivator can be controlled under different conditions. Further, the method entails transforming a second plant with a member of a second pool of receptor vectors. The receptor construct comprises a transactivator binding site for binding a transactivator. The transactivator binding site is operably linked to a gene of interest which permits overexpression (for example, by using sense constructs) or underexpression (for example, by using antisense constructs) of the gene when transactivator expression is turned on. Of particular interest are genes that affect polygenic traits, such as regulatory genes.

Then specific crosses are made in a combinatorial manner between individual members from the two pools of plants: a first pool engineered to contain specific regulatory sequences (such as promoters) and a second pool engineered to contain genes of interest (such as regulatory genes). The gene of interest is expressed only under control of each different promoter in the progeny plant, providing the same effect as if each plant had been transformed initially with the specific gene-promoter combination. In this manner large numbers of specific gene-promoter combinations can therefore be made and the effect on transcription expression and trait improvement investigated with minimal time and expense.

This method is an improvement of the method described in Liu et al. U.S. Pat. No. 5,968,793 and Guyer et al. (1998) Genetics 149: 633–639, that describe methods wherein both donor and receptor vectors are transformed into the same plant to regulate gene expression and to observe trait improvements in a plant. Our method provides a greater degree of flexibility and speed for observing the effects of selective gene expression on the traits of a plant.

Trait improvements for any plant may be investigated by this method. The plant may be a crop plant such as soybean, wheat, corn, potato, cotton, rice, oilseed rape (including canola), sunflower, alfalfa, sugarcane and turf; or a fruit or vegetable plant, such as apple, banana, blackberry, blueberry, strawberry, and raspberry, cantaloupe, carrot, cauliflower, coffee, cucumber, eggplant, grape, honeydew, lettuce, mango, melon, onion, papaya, peas, peppers, pineapple, spinach, squash, sweet corn, tobacco, tomato, watermelon, rosaceous fruits (such as peach, cherry and plum) and vegetable brassicas (such as broccoli, cabbage, cauliflower, brussel sprouts and kohlrabi). Other crops, fruits and vegetables whose trait may be improved include barley, sorghum, currant, avocado, citrus fruits such as oranges, lemons, grapefruit and tangerines, artichoke, currant, cherries, nuts such as the walnut and peanut, pear, endive, leek, roots, such as arrowroot, beet, cassava, turnip, radish, yam, sweet potato and beans.

One embodiment of the present invention is illustrated in the FIGURE. An activator plant is grown from seed derived from plants that have been transformed with a construct containing one of ten different promoters linked to a transactivator gene (in this FIGURE a fusion of the Lac I binding domain and the Gal4 transactivation domain). A target plant is transformed with a construct containing the LacI binding sites linked to one of over 1,700 transcription factor genes that have been identified from *Arabidopsis thaliana*. The target plant does not express the plant transcription factor unless the transactivator is present. Only after activator and target plants are crossed is the plant transcription factor over-or-underexpressed by having the transactivator bind to its binding site on the plant transcription factor gene construct. Thus, the traits associated with selective or constitutive over-or-underexpression of a plant transcription factor in plant tissue, depending on the promoter, can be easily controlled and screened.

The Donor Construct

The donor construct comprises a recombinant polypeptide sequence which encodes a DNA binding domain fused to a transcription activation domain. This recombinant polynucleotide is the transactivator. A DNA binding domain is a sequence that binds to DNA with some degree of specificity. A common feature of some activation domains is that they are designed to form amphiphilic alpha helices with excess positive or negative charge (Giniger and Ptashne (1987) *Nature* 330:670–672, Gill and Ptashne (1987) *Cell* 51:121–126, Estruch et al (1994) *Nucl. Acids Res.* 22:3983–3989). Examples include the transcription activation region of VP16 or GAL4 (Moore et al. (1 998) *Proc. Natl. Acad. Sci. USA* 95: 376–381; and Aoyama et al. (1995) *Plant Cell* 7:1773–1785), peptides derived from bacterial sequences (Ma and Ptashne (1987) *Cell* 51; 113–119) and synthetic peptides (Giniger and Ptashne, supra). Exemplary transactivators are those described in Brent and Ptashne, U.S. Pat. No. 4,833,080, herein incorporated by reference or in Hasselhoff and Hodge, WO97/30164.

Various promoter sequences are available which may be used to control expression of the transactivator. Such promoters may be utilized to initiate transcription of a nucleic acid sequence of interest operably linked to the promoter region.

For constitutive expression in plants viral promoters may be utilized in plant expression vectors. These include the 35S RNA and 19S RNA promoters of CaMV (Brisson, et al., *Nature,* 310:511, 1984, Odell, et al., *Nature,* 313:810, 1985); the promoter from Figwort Mosaic Virus (FMV) (Gowda, et al., *J. Cell Biochem.,* 13D:301, 1989) and the coat protein promoter of TMV (Takamatsu, et al., *EMBO J.* 6:307, 1987). Additional promoters include the nopaline synthase promoter (An et al., (1988) *Plant Physiol.* 88:547); and the octopine synthase promoter (Fromm et al., (1989) *Plant Cell* 1: 977).

The donor construct may include one or more inducible promoters. Examples of inducible promoters useful in plants include those induced by chemical means, such as the yeast metallothionein promoter which is activated by copper ions (Mett, et al., (1993) *Proc. Natl. Acad. Sci., U.S.A.,* 90:4567); In2-1 and In2-2 regulator sequences which are activated by substituted benzenesulfonamides, e.g., herbicide safeners (Hershey, et al., (1991) *Plant Mol. Biol.,* 17:679): and the GRE regulatory sequences which are induced by glucocorticoids (Schena, et al. (1991), *Proc. Natl. Acad. Sci., U.S.A.,* 88:10421). Plant promoters also include the light-inducible promoter from the small subunit of ribulose bis-phosphate carboxylase (ssRUBISCO) (Coruzzi, et al., (1984) *EMBO J.,* 3:1671; Broglie, et al., (1984) *Science,* 224:838), promoters regulated by heat (Callis et al., (1988) *Plant Physiol.* 88:965; Ainley, et al. (1993) *Plant Mol. Biol.* 22: 13–23; hormones, such as abscisic acid (Marcotte et al., (1989) *Plant Cell* 1: 969); wounding (e.g., wun1, Siebertz et al., (1989) *Plant Cell* 1: 961; and chemicals such as methyl jasminate or salicylic acid (Gatz et al., (1997) *Ann. Rev. Plant Physiol. Plant Mol. Biol.* 48: 89–108).

Tissue specific promoters may also be utilized for expression of genes in plants. Tissue specific promoters useful in transgenic plants include the cdc2a promoter and cyc07 promoter (Ito, et al.,(1994) *Plant Mol. Biol.,* 24:863; Martinez, et al. (1992) *Proc. Natl. Acad. Sci. USA,* 89:7360; Medford, et al., (1991) *Plant Cell,* 3:359; Terada, et al. (1993) *Plant Journal,* 3:241;. Wissenbach, et al., (1993) *Plant Journal,* 4:411). Additional tissue specific promoters that are utilized in plants include the histone promoter (Atanassova, et al., (1992) *Plant Journal,* 2:291); the cinnamyl alcohol dehydrogenase (CAD) promoter (Feuillet, et al., (1995) *Plant Mol. Biol.,* 27:651); the mustard CHS1 promoter (Kaiser, et al., (1995) *Plant Mol. Biol.,* 28:231); the bean grp 1.8 promoter (Keller, et al., (1994) *Plant Mol. Biol.,* 26:747); the PAL1 promoter (Ohl, et al. (1990) *Plant Cell,* 2:837); and the chalcone synthase A promoter (*Plant Mol. Biol.,* (1990)15:95–109). In addition, the timing of the expression can be controlled by using promoters such as those acting at senescence (Gan and Amasino (1995) *Science* 270: 1986–1988); or late seed development (Odell et al. (1994) *Plant Physiol.* 106:447–458).

Other promoters include root-specific promoters such as root-specific promoters disclosed in U.S. Pat. Nos. 5,618, 988, 5,837,848 and 5,905,186 or the prxEa promoter in Wanapu and Shinmyo (1996) *Ann. N.Y. Acad. Sci.* 782:107–113 or Miao et al. (1991) *Plant Cell* 3:11–22 or Hirel et al. (1992) *Plant Mol. Biol.* 20:207–218), seed-specific promoters such as the napin, phaseolin or DC3 promoter described in U.S. Pat. No. 5,773,697, the oleate 12-hydroxylase: desaturase promoter from Lesquerella (Broun et al (1998) *Plant J.* 13:201–210), the oleosin promoter or *Arabidopsis* (Plant et al (1994) *Plant Mol. Biol.* 25:193–205), a zein promoter of maize (Russel et al (1997) *Transgenic Res.* 6:157–168), the glutelin promoters of rice (Washida et al. *Plant Mol Biol.* (1999) 40:1–12) and maize (Thomas et al (1990) *Plant Cell* 2:1171–1180), fruit specific promoters such as those active during fruit ripening (such as the dru 1 promoter (U.S. Pat. No. 5,783,393), or the 2A11 promoter (U.S. Pat. No. 4,943,674) and the tomato polygalacturonase promoter (Bird et al. (1988) *Plant Mol. Biol.* 11:651), pollen-active promoters such as PTA29, PTA26 and PTA13 (U.S. Pat. No. 5,792,929), promoters active in vascular tissue (Ringli and Keller (1998) *Plant Mol. Biol.* 37:977–988), flower-specific (Kaiser et al, (1995) *Plant Mol. Biol.* 28:231–243), pollen (Baerson et al. (1994) Plant Mol. Biol. 26:1947–1959), carpels (Ohl et al. (1990) *Plant Cell* 2:837–848), pollen and ovules (Baerson et al. (1993) *Plant Mol. Biol.* 22:255–267).

Preferred inducible or tissue-specific promoters include Rd 29a (Yamaguchi-Shinozaki and Shinozaki (1993) *Plant Physiol.* Mar; 101:1119–20), LTP1 (Thoma et al. (1994) *Plant Physiol,* 105(1):35–45), STM (Long et al. (1996) *Nature.* 1996 379:66–9), rbcS (Krebbers (1 988) *Plant Mol Biol.* 11: 745–759), sucrose synthase (Martin et al. (1993) *Plant J.* 4:367–77), EIR1 (Luschnig et al. (1998) *Genes Dev.* 12:2175–87), IL (Bernhard, and Matile, GenBank Accession Number M83534), PR1 (Lebel et al. (1998) *Plant J.* 16:223–33), AGL1 (Ma et al. (1991) *Genes* 5:484–95), AP1 (Mandel et al. (1992) 360:273–7), E4 (Cordes et al. (1989) *Plant Cell.* 1(10):1025–34), or GL2 (Rerie et al. (1994) *Genes Dev.* 8(12):1388–99).

The donor construct may also include additional sequences such as selectable markers linked to a constitutive promoter for selecting plants containing the donor construct in field trials or tissue culture. These may include the acetoacetate synthase gene for chlorosulfuron resistance or the gene that confers resistance to cyanamide.

Plant transformation constructs may also include RNA processing signals, for example, introns, which may be positioned upstream or downstream of the open reading frame sequence (ORF). In addition, the expression constructs may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

The Receptor Construct

The receptor construct comprises one or more DNA binding sites for one of the transactivators described above, such as those disclosed in U.S. Pat. No. 4,833,080, operably linked to a gene of interest, such as a transcription factor, phosphatase or kinase. The transcription factors contained in the construct may be derived from one or more of the transcription factor families described below.

The plant transcription factors may belong to one of the following transcription factor families: the AP2 (APETALA2) domain transcription factor family (Riechmann and Meyerowitz (1998) *J. Biol. Chem.* 379:633–646); the MYB transcription factor family (Martin and Paz-Ares, (1997) *Trends Genet.* 13:67–73); the MADS domain transcription factor family (Riechmann and Meyerowitz (1997) *J. Biol. Chem.* 378:1079–1101); the WRKY protein family (Ishiguro and Nakamura (1994) *Mol. Gen. Genet.* 244:563–571); the ankyrin-repeat protein family (Zhang et al. (1992) *Plant Cell* 4:1575–1588); the zinc finger protein (Z) family (Klug and Schwabe (1995) *FASEB J.* 9: 597–604); the homeobox (HB) protein family (Duboule (1994) *Guidebook to the Homeobox Genes,* Oxford University Press); the CATT-element binding proteins (Forsburg and Guarente (1989) *Genes Dev.* 3:1166–1178); the squamosa promoter binding proteins (SPB) (Klein et al. (1996) *Mol. Gen. Genet.* 1996 250:7–16); the NAM protein family (Souer et al. (1996) *Cell* 85:159–170); the IAA/AUX proteins (Rouse et al. (1998) *Science* 279.1371–1373); the HLH/MYC protein family (Littlewood et al. (1994) *Prot. Profile* 1:639–709); the DNA-binding protein (DBP) family (Tucker et al. (1994) *EMBO J.* 13:2994–3002); the bZIP family of transcription factors (Foster et al. (1994) *FASEB J.* 8:192–200); the Box P-binding protein (the BPF-1) family (da Costa e Silva et al. (1993) *Plant J.* 4:125–135); the high mobility group (HMG) family (Bustin and Reeves (1996) *Prog. Nucl. Acids Res. Mol. Biol.* 54:35–100); the scarecrow (SCR) family (Di Laurenzio et al. (1996) *Cell* 86:423–433); the GF14 family (Wu et al. (1997) *Plant Physiol.* 114:1421–1431); the polycomb (PCOMB) family (Kennison (1995) *Annu. Rev. Genet.* 29:289–303); the teosinte branched (TEO) family (Luo et al. (1996) *Nature* 383:794–799; the ABI3 family (Giraudat et al. (1992) *Plant Cell* 4:1251–1261); the triple helix (TH) family (Dehesh et al. (1990) *Science* 250:1397–1399); the EIL family (Chao et al. (1 997) *Cell* 89:1133–44); the AT-HOOK family (Reeves and Nissen (1990) *Journal of Biological Chemistry* 265:8573–8582); the S1FA family (Zhou et al. (1995) *Nucleic Acids Res.* 23:1165–1169); the bZIPT2 family (Lu and Ferl (1995) *Plant Physiol.* 109:723): the YABBY family (Bowman et al. (1999) *Development* 126:2387–96); the PAZ family (Bohmert et al. (1998) *EMBO J.* 17:170–80): a family of miscellaneous (MISC) transcription factors including the DPBF family (Kim et al. (1 997) *Plant J.* 11:1237–1251) and the SPF1 family (Ishiguro and Nakamura (1994) *Mol. Gen. Genet.* 244:563–571); the golden (GLD) family (Hall et al. (1998) *Plant Cell* 10:925–936).

Other transcription factors may be identified by screening polynucleotide or polypeptide sequence databases, such as GenBank, using using sequence alignment methods and homology calculations, such as those described in Altschul et al. (1994) *Nature Genetics* 6: 119–129. For example, the NCBI Basic Local Alignment Search Tool (BLAST) (Altschul et al. (1990) Basic local alignment search tool. *J. Mol. Biol.* 215:403–410) is available from several sources, including the National Center for Biotechnology Information (NCBI, Bethesda, Md., for use in connection with the sequence analysis programs blastp, blastn, blastx, tblastp, tblastn and tblastx. Alternatively, a program that identifies particular sequence motifs may be employed along with specific characteristic consensus sequences, such as FIND PATTERN (GCG, Madison, Wis.).

Exemplary transcription factors that can be employed in the invention include those disclosed in Zhang et al. U.S. application Ser. No. 09/394,519, filed Sep. 13, 1999, entitled "Plant Gene Sequences I", Keddie et al. U.S. application Ser. No. 09/506,720, filed Feb. 17, 2000, entitled "Plant Gene Sequences II", Keddie et al. U.S. application Ser. No. 09/533,030, filed Mar. 22, 2000, entitled "Polynucleotides for Seed Trait Alteration", Cai-Zhong et al. U.S. application Ser. No. 09/533,392, filed Mar. 22, 2000, entitled "Polynucleotides for Root Trait Alteration", Heard et al. U.S. application Ser. No. 09/533,029, filed Mar. 22, 2000, entitled "Disease-Induced Polynucleotides", Samaha et al. U.S. application Ser. No. 09/532,591, filed Mar. 22, 2000, entitled "Stress-Induced Polynucleotides", and Riechmann et al. U.S. application Ser. No. 09/533,648, filed Mar. 22, 2000, entitled "Polynucleotides for Flower Trait Alteration".

The transcription factors encompass the naturally occurring sequences as well as non-naturally occurring sequences which are derivatives of the transcription factors described above. For example, the amino acid sequence encoding the binding protein may be a naturally occurring sequence such as the ones shown above or a non-naturally occuring sequence using domains of transcription factors described above fused in frame, but not necessarily adjacent, with functional domains derived from other sequences or sources. Additionally, the invention includes polypeptides derived from shuffling regions of transcription factors described above by methods described in Minshull and Stemmer, U.S. Pat. No. 5,837,458, entitled "Methods and Compositions for Cellular and Metabolic Engineering" and Stemmer and Crameri, U.S. Pat. No. 5,811,238, entitled "Methods for Generating Polynucleotides having Desired Characteristics by Iterative Selection and Recombination".

The particular arrangement of the transcription factor sequence in the transformation vector will be selected according to the type of expression of the sequence that is desired. Where enhanced transcription factor activity is desired in the plant, a transcription factor coding sequence may be operably linked to a constitutive high-level promoter such as the CaMV 35S promoter. Generally, this will require the full length sequence encoding the transcription factor. In contrast, a reduction of transcription factor activity in the transgenic plant may be obtained by introducing into plants antisense constructs based on the transcription factor cDNA. For antisense suppression, the transcription factor cDNA is arranged in reverse orientation relative to the promoter sequence in the transformation vector. The introduced sequence need not be the full length transcription factor cDNA or gene, and need not be exactly homologous to the transcription factor cDNA or gene found in the plant type to be transformed. Generally, however, where the introduced sequence is of shorter length, a higher degree of homology to the native transcription factor sequence will be needed for effective antisense suppression.

Constructs in which RNA encoded by the transcription factor cDNA (or variants thereof is overexpressed may also be used to obtain co-suppression of the endogenous transcription factor gene in the manner described in U.S. Pat. No. 5,231,020 to Jorgensen. Such co-suppression (also termed sense suppression) does not require that the entire transcription factor cDNA be introduced into the plant cells, nor does it require that the introduced sequence be exactly identical to the endogenous transcription factor gene. However, as with antisense suppression, the suppressive efficiency will be enhanced as (1) the introduced sequence is lengthened and (2) the sequence similarity between the introduced sequence and the endogenous transcription factor gene is increased. Alternatively, supression on a transcription gene activity may be obtained by double stranded RNA-mediated interference (Voinnet, et al., (1998) *Cell* 95, 177–187, Waterhouse, et al. (1998) *Proc. Natl. Acad. Sci. USA* 95, 13959–13964).

The receptor vector may also include additional sequences such as selectable markers linked to a constitutive promoter for selecting plants containing the activatorconstruct in field trials or tissue culture. These may include the acetoacetate synthase gene for chlorosulfuron resistance or the gene that confers resistance to cyanamide.

Any of the identified sequences may be incorporated into a cassette or vector for expression in plants. A number of expression vectors suitable for stable transformation of plant cells or for the establishment of transgenic plants have been described including those described in Weissbach and Weissbach, (1989) *Methods for Plant Molecular Biology*, Academic Press, and Gelvin et al., (1990) *Plant Molecular Biology Manual*, Kluwer Academic Publishers. Specific examples include those derived from a Ti plasmid of *Agrobacterium tumefaciens*, as well as those disclosed by Herrera-Estrella, L., et al., (1983) *Nature* 303: 209, Bevan, M., *Nucl. Acids Res.* (1 984) 12: 8711–8721, Klee, H. J., (1985) *Bio/Technology* 3: 637–642, for dicotyledonous plants.

Alternatively, non-Ti vectors can be used to transfer the DNA into plants and cells by using free DNA delivery techniques. Such methods may involve, for example, the use of liposomes, electroporation, microprojectile bombardment, silicon carbide wiskers, and viruses. By using these methods transgenic plants such as wheat, rice (Christou, P., (1991) *Bio/Technology* 9: 957–962) and corn (Gordon-Kamm, W., (1990) *Plant Cell* 2: 603–618) can be produced. An immature embryo can also be a good target tissue for direct DNA delivery techniques by using the particle gun (Weeks, T. et al., (1993) *Plant Physiol.* 102: 1077–1084; Vasil, V., (1993) *Bio/Technology* 10: 667–674; Wan, Y. and Lemeaux, P., (1994) *Plant Physiol.* 104: 37–48, and for *Agrobacterium*-mediated DNA transfer (Ishida et al., (1 996) *Nature Biotech.* 14: 745–750).

Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally-or developmentally-regulated, or cell- or tissue-specific expression), a transcription initiation start site, an RNA processing signal (such as intron splice sites), a transcription termination site, and/or a polyadenylation signal.

Transformation

Standard techniques may be used to transform plants with the above described vectors to overexpress or underexpress the genes of interest in plants in order to understand a gene's effect on a plant's phenotype. Additionally, combinations of transactivator or donor rvectors may be used to transform plants to understand the contribution of multiple genes of interest to a trait.

Exemplary plants to be transformed may be any higher plant, including monocotyledonous and dicotyledenous plants. Suitable protocols are available for *Leguminosae* (alfalfa, soybean, clover, etc.), *Umbelliferae* (Carrot, celery, parsnip), *Cruciferae* (cabbage, radish, rapeseed, broccoli, etc.), *Curcurbitaceae* (melons and cucumber), *Gramineae* (wheat, corn, rice, barley, millet, etc.), *Solanaceae* (potato, tomato, tobacco, peppers, etc.), and various other crops See protocols described in Ammirato et al. (1984) *Handbook of Plant Cell Culture—Crop Species*. Macmillan Publ. Co. Shimamoto et al. (1989) *Nature* 338:274–276; Fromm et al. (1990) *Bio/Technology* 8:833–839; and Vasil et al. (1990) *Bio/Technology* 8:429–434.

Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; microprojectile bombardment of plant cells; vacuum infiltration; and *Agrobacterium tumeficiens* (AT) mediated transformation.

Successful examples of the modification of plant characteristics by transformation with cloned cDNA sequences which serve to illustrate the current knowledge in this field of technology, and which are herein incorporated by reference, include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042. Successful transformation of woody species, such as poplar and aspen transformation using *Agrobacterium tumefaciens*, can be performed as described by De Block, (1990) *Plant Physiol.* 93:1110–1116. Other woody species that may be transformed include pine. Of particular interest is the transformation of tomatoes, for example as illustrated in Filatti et al. U.S. Pat. No. 5,565,347.

Following transformation and regeneration of plants with the transformation vector, transformed plants may be selected using a dominant selectable marker incorporated into the transformation vector. Typically, such a marker will confer antibiotic or herbicide resistance on the seedlings of transformed plants, and selection of transformants can be accomplished by exposing the seedlings to appropriate concentrations of the antibiotic or herbicide.

Crossing

Plants transformed with any of the donor vector may be crossed with plants transformed with any of the receptor vectors as described in the FIGURE. Plants transformed with a receptor vector for a specific transcription factor (in a sense or antisense configuration) can be crossed with a variety of plants transformed with donor vectors comprising a variety of different promoters, including constitutive, inducible or tissue-specific vectors to investigate the effects of transcription factor expression throughout the plant, under specific conditions such as environmental stresses, disease, or the like, in specific tissues, such as seeds, roots, flowers, stems, leaves, fruits or the like. Seeds are collected and hybrid plants are grown to maturity. These plants can then be screened to identify plants with valuable traits.

These plants may be grown in the presence of first and second herbicide resistant selectable markers. Seed obtained from herbicide resistant regenerated plants may be crossed further to generate later generation hybrid plants. Additional details in crop breeding techniques, in particular those for tomatoes are described in U.S. Pat. No. 5,817,913, herein incorporated by reference.

Additionally, the present invention is a plant breeding kit. In this manner, seed or plants are provided, wherein a first pool of seed or plants is provided that are transformed with the donor vector and a second pool of seed or plants is provided that are transformed-with the receptor vector. Then plant breeders can cross plants from first and second pools as described above to breed plants with improved traits.

The following-examples are provided to better elucidate the practice of the present invention and should not be interpreted in any way to limit the scope of the present invention. Those skilled in the art will recognize that various modifications can be made to the methods and genes described herein without departing from the spirit and scope of the present invention.

EXAMPLES

The invention is illustrated by Examples wherein six different donor vectors having a constitutive, an inducible promoter or a tissue specific promoter operably linked to either of two different transactivators are prepared. Additionally the invention is illustrated by the preparation of eight different receptor vectors comprising a transactivator binding site operably linked to a transcription factor. Donor and receptor vectors are then transformed into different tomato plants. Transformed tomato plants having different donor vectors are then crossed with transformed tomato plants having different receptor vector. Improved traits can be screened for in the progeny.

Example 1

Cloning of Promoters in Donor Vector

The plasmid vector pMEN020 was the vector used for donor and receptor vector construction. The pMEN020 plasmid construct is a binary cloning vector that contains both *E. coli* and *Agrobacterium tumefaciens* origins of DNA replication but no vir genes encoding proteins essential for the transfer and integration of the target gene inserted in the T-DNA region. PMEN020 requires the trfA gene product to replicate in *Agrobacterium*. The strain of *Agrobacterium* containing this trfA gene is called the ABI strain and is described in U.S. Pat. Nos. 5,773,701 and 5,773,696. This cloning vector serves as an *E. coli—Agrobacterium tumefaciens* shuttle vector. All of the cloning steps are carried out in *E. coli* before the vector is introduced into ABI strain of *Agrobacterium tumefaciens*.

Two different sets of constructs, which are based on bacterial DNA binding proteins LexA and LacI, respectively, were prepared. For the LexA system, the construct was prepared in two steps. First, an intermediate construct was generated containing the LexA protein and the gal4 activation domain. In the intermediate construct, four fragments were generated separately and fused by overlap extension PCR. The first fragment was the 35S minimal promoter and omega translation enhancer; The fragment was amplified from construct SLJ4D4 (Jones et al 1992 *Transgenic Research* 1:285) using primers O11731 (SEQ ID No. 1): GCCCAAGCTTTGAGCTCCGCGGCCGCAAGACCCT TCCTCTATATAAGGAAGTTC A and O11733 (SEQ ID No. 2): ACGCTTCCATGGTAATTGTAAATGTAATTG TAATGTTGT.

The second fragment was the lexA gene of *E coli*; it was amplified from plasmid pLexA (Clontech, Palo Alto, Calif.) using primers O11732 (SEQ ID No. 3): TTACAATTAC- CATGGAAGCGTTAACGGCCAGGCAACAAGA and O117717 (SEQ ID No. 4): TATTCCCACTTTGATTAAAA TTGGGGAATTCCAGCCAGTCGCCGT.

The third fragment was the gal4 transcription activation domain; it was amplified from pGAD424 (aa 768–881, Clontech) by primers O11715 (SEQ ID No. 5): GGCTG- GAATTCCCCAATTAATCAAAGTGGGAA and O11718 (SEQ ID No. 6): AAGCTCTAGCTACTCTTTTTTTGGG TTTGGTGGGGT. The fourth fragment was the E9 transcription terminator (Fluhr et al 1986 *EMBO J.* 5:2063); it was amplified from pMON10098 using primers O11716 (SEQ ID No. 7): AAGAGTAGCTAGAGCTTTCGTTCG TATCA and O11719 (SEQ ID No. 8): TGCTCTAGATTGA TGCATGTTGTCAATCA. The four fragments were fused together by PCR using primers O11731 and O11719. Note that restriction enzyme digest sites HindIII and XbaI were added to the ends of O11731 and O11719, respectively.

Inserts from the intermediate construct were cloned into the HindIII and BamHI sites of pMEN020.

The lacI system was constructed in a similar fashion as the lexA system, in two steps. The translation initiation of the lacI gene was changed to ATG from GTG and a mutation at position 17 (Y to H, Lehming et al 1987 *EMBO J* 6:3145) was introduced. The lacI gene was cloned from *E coli* genomic DNA by PCR amplification using primers O16400 (SEQ ID No. 9): CATGCCATGGAACCAGTAACGTTAT ACGATGTCGCAGAGTATGCCGGTGTCTCTCATCAG ACCGTTTCCCGCG) and O16401 (SEQ ID No. 10): GGG GAATTCAAGGGTGGTTTTTCTTTTCACCAGTGA. Note that NcoI and EcoRI sites were introduced with O16400 and O16401, respectively. The lacI coding region, which is defined by the NcoI and EcoRI sites, was used to replace lexA coding region in the previous intermediate construct. Insets from the two intermediate constructs were cloned into the HindIII and BamHI sites of pMEN020 in a three way ligation.

A multiple cloning site was added upstream of the LacI (LexA)/gal4 fusion protein by O11731 to facilitate the cloning of promoter fragments. In order to test the functionality of the system, full 35S promoters may be cloned upstream of the LacI (LexA)/gal4 fusion protein by using restriction enzymes Hind III and NotI. Inducible promoters from plant genomic DNAs can be isolated by PCR amplification using primers flanking the promoter region and containing suitable restriction sites for cloning into the activation vector. For example, the rd29a gene was characterized by Shinozaki's group in Japan (Yamaguchi- Shinozaki and Shinozaki (1993) *Plant Physiol.* 101: 1119–1120). The rd29a gene expression is induced by desiccation, salt stress and exogenous ABA treatment (Yamaguchi-Shinozaki and Shinozaki (1993) *Plant Physiol.* 101: 1119–1120(1993); Ishitani et al. (1998) *Plant Cell* 10: 1151–1161).

A genomic clone carrying the rd29a promoter was identified by using rd29a as a search word at the www site of NCBI. The sequence for the rd29a promoter is located in the region between nucleotide positions 3892 to 5390 (Accession No. D13044). The following two primers were designed to amplify this promoter region from *Arabidopsis* genomic DNA: rd29a-primer1 (SEQ ID No. 11): GCCCA AGCTTGGTTGCTATGGTAGGGACTAT; and rd29a- primer2 (SEQ ID No. 12): ATAAGAATGCGGCCGCG AGAGATAAAGGGACACGTATGAAGC. The rd29a- primer1 includes a Hind III. (AAGCTT) restriction site near the 5'-end of the primer and rd29a-primer2 has a NotI (GCGGCCGC) restriction site near 5'-end of the primer.

Total genomic DNA was isolated from *Arabidopsis thaliana* (ecotype Colombia) by using the CTAB method (Ausubel et al. (1992) *Current Protocols in Molecular Biology* (Greene & Wiley, New York)). Ten nanograms of the genomic DNA was used as a template in a PCR reaction under conditions suggested by the manufacturer (Boehringer Mannheim). The reaction conditions that were used in this PCR experiment are as follows: Segment 1: 94° C., 2 minutes; Segment 2: 94° C., 30 seconds; 60° C., 1 minute; 72° C., 3 minutes, for a total of 35 cycles; Segment 3: 72° C. for 10 minutes. A PCR product of 1525 base pair is expected. The PCR products were subject to electrophoresis in a 0.8% agarose gel and visualized by ethidium bromide staining. The DNA fragments containing the inducible promoter were excised and purified using a Qiaquick gel extraction kit (Qiagen, Calif.). The purified PCR product can then be digested with HindIII and NotI, and cloned into the HindIII and NotI sites of LexA and LacI based donor vectors.

Similarly, tissue specific promoters from plant genomic DNAs can also be isolated by PCR amplification. For example, the non-specific lipid transfer protein (or LTP1) promoter is specific for the epidermis layer of plants (Thoma et al, *Plant Physiol.* 105(1) 35–45 (1994)). The sequence for the LTP1 promoter is located in the region between nucleotide positions 1 to 1130 (Accession No. M80567). The following two primers were designed to amplify this promoter region from *Arabidopsis* genomic DNA: LTP1- primer1 (SEQ ID No. 13): GCCCAAGCTTGATTAACT- TGCATTACAGTTGGGAAAGT; and LTP1-primer2 (SEQ ID No. 14): ATAAGAATGCGGCCGCGGTACGTATAT- GTTATGTGGTGTGAATG. The LTP1-primer1 includes a Hind III (AAGCTT) restriction site near the 5'-end of the primer, and LTP1-primer2 has a NotI (GCGGCCGC) restriction site near 5'-end of the primer. The promoter fragment can then be cloned into the activation vector as described above Example 2

Construction of Receptor Vector

The receptor vector includes a corresponding binding region for the transactivator factor prepared above, in this case a LexA or LacI binding site, and a gene of interest, such as a transcription factor.

Two versions of the cloning vector will be built, one each for Lexa and LacI, respectively. For the Lexa version, eight copies of the Lexa binding site and the 35S minimal promoter will be cloned upstream of the E9 terminator. To this end, two fragments will be generated and then fused together by overlap PCR. The first fragment will be generated by primers O16417 (SEQ ID No. 15): GGCCCAAGCTTA- CATATCCATATCTAATCTTACCT and O11723, using the lexA_OP construct (described in the previous section) as template. The second will be generated by primers O11721 and O16416 (SEQ ID No. 16): CTAGAGGATCCGGTAC GAGGCCTGTCTA, using pMEN20 as template. The two PCR products can be assembled together by PCR using primers O16417 and O16416. Note that HindIII recognition site is designed in the 5' of O16417, and the pMEN20 multiple cloning site will be included in the final product. This product will be ligated into the HindIII and BamHI sites of a modified pMEN20, which should have a different selectable marker (e.g. glyphosate resistance marker). The lacI version will be identical to the above, except that two copies of the lacI binding site will replace the lexa binding site. The lacI binding sites will be included in O16415 (SEQ ID No. 17): GGCCCAAGCTTAATTGTGAGCGCTCACA ATTCATGAATTGTGAGCGCTCACAATT PCR product by primers O16415 and O16416, using pMEN20 as template, will include two copies of the lacI binding sites, the 35S minimal promoter, and the multiple cloning site of pMEN20.

The CBF1 coding region can be amplified by PCR using primers O11700 (SEQ ID No. 18): ACGCGTCGACGACT-GAGAACTCTAGTAACTACGTA and O11702 (SEQ ID No. 19): ATAAGAATGCGGCCGCCGACTATCGAAT ATTAGTAACTCCA.

The resulting PCR product, approximately 780 bp, can be digested with SalI and NotI and cloned into the SalI and NotI sites of the receptor vector. Additionally, a seed specific transcription factor ATML1 (Lu et al. (1996) during embryonic pattern formation and defines a new class of homeobox genes *Plant Cell* 8(12):2155–68, GenBank Accession No. U37589) can be amplified by PCR using primers O5184 (SEQ ID No. 20): CGGGGTACCCTTCTCCACAAGT AAGGGAACCAGA and O5185 (SEQ ID No. 21): ATAA GAATGCGGCCGCCCTCCCCTTTCACTCTTACCT TCCGAA. The resulting PCR product, approximately 2,400 bp, can be digested with KpnI and NotI and cloned into the KpnI and NotI sites of the receptor vector. Furthermore, a root specific transcription factor PRL2 (Newman, et al. (1994) Plant Physiol. 106, 1241–1255) was obtained from a full length expressed sequence tag (GenBank Accession No. R86816). The cDNA can be isolated from the library vector by using the SalI and NotI enzymes, and then it can be cloned into the SalI and NotI sites of the receptor sites. In a fourth example, a ATHB-12 (Lee et al. (1998) *Plant Mol Biol*. 37:377–84) was subcloned into the receptor vector by using SalI and NotI as previously described.

Example 3

Transformation of Tomatoes

Tomato transformations are performed using the following procedure. Tomato seeds are sterilized in 50% bleach solution for 20–30 minutes and rinsed at least 3 times with sterile water. The seed are placed in magenta jars that contain the following media: 1× MS Salts, 1× Gamborg's Vitamins, 2% sucrose, and 0.8% phytagar. The seeds are germinated for 7–10 days at 25° C. with 16 hours of light. *Agrobacterium* from glycerol stock is inoculated into 5 ml of LB or YEP with the appropriate antibiotics, and the culture grown at 28° C. overnight with shaking at 250 rpm. When the optimal OD600 is reached (between 1.0 and 1.5), the bacteria are spun down and resuspended in liquid germination media to a concentration of 0.2 OD600. The cotyledons from 7–10 days old seedlings are cut into 0.5 cm pieces, and transferred to a co-cultivation plate with (D1-) media containing the following: 1× MS salts, 1× Gamborg's Vitamins, 3% glucose, 1 mg/L zeatin, 0.8% (w/v) phytagar, pH to 5.8, and 375 uM Acetosyringone. 10–15 ml of diluted Agro solution are poured over the explants and incubated for 40 min. The explants are turned upside down on (D1-) cocultivation media for 48 hours at 25° C. with 16 hours of light. About 20–25 explants are transferred onto D1 plates that contain the following media: 1× MS salts, 1× Gamborg's Vitamins, 3% glucose, 1 mg/L zeatin, 0.8% (w/v) phytagar, pH 5.8, 300 u/ml Timentin, and selected for the construct. After 10–15 days, whole explants are transferred to D2 plates containing the following: 1× MS salts, 1× Gamborg's Vitamins, 3% glucose; 0.1 mg/L zeatin, 0.8% (w/v) phytagar, pH 5.8, 300 u/ml Timentin, and appropriate selection for the construct. And from then on, every 2–3 weeks the explants are transferred to fresh D2 plates. Shoots form in a few weeks. When the shoots are 1–1.5 cm tall, the shoots are cut off from the calli and transferred to a medium containing the following: 1× MS salts, 1× Gamborg's Vitamins, 3% glucose, 0.8% (w/v) phytagar, pH 5.8, 300 u/ml Timentin, and appropriate selection for the construct. Rooted shoots are transferred to soil in 2-inch pots inside Magenta jars. Once the plants have established in the soil, they can be transplanted to bigger pots and tested for the presence of the transgene.

Tomato Breeding for Trait Improvement

Using the above protocol, a first pool of tomatoes can be transformed with vectors comprising a constitutive promoter (35S promoter) or an inducible promoter (rd29a or Itp1) in combination with either lexA/Gal4 or lacI/Gal4 transactivators. A second pool of tomatoes can be transformed with vectors comprising lexA or lacI binding sites in combination with either CBF, PRL2, ATML1 or ATHB-1.

First and second pools of tomato plants are components of the plant breeding kit.

The following definitions are employed: T0: the initial transgenic plant produced from tissue culture, S1–S4 or F1–F4: The S numbers are for self pollinations, while the F number is a cross between two lines. For example, a T0 plant can be both self pollinated (S1 seeds produced) and outcrossed to an donor line initially (F1 seeds produced). F1S2 would be the selfed progenies of a F1 parent.

The transformed T0 plants will be grown to maturity in greenhouses (the plants can be scored with cyanamide herbicides if escapes are a problem). Some of the flowers will be crossed to T0 plants containing the donor vector. (The F1 progeny of this cross will be segregating for both genes). Several flowers will be crossed to obtain at least 100 seeds. The self pollinated seeds (S1) will be saved for later crosses to different activator promoters.

The F1 progeny will be screened by spraying chlorsulfuron and cyanamide to find the progeny containing both the donor (chlorsulfuron resistant) and receptor (cyanamide resistant) vectors (heterozygous for both). Both chlorsulfuron resistance and cyanamide resistance are dominant in their effects, so phenotypes resistant to both herbicides and thus containing both genes should be observable in the F1progeny. The presence of two distinguishable herbicidal markers greatly facilitates determining the genotype.

The F1 progeny may be screened by RT-PCR. F1S2 plants are segregating for both the activator and-receptor genes. F1S2 plants are grown and sprayed with chlorsulfuron and cyanamide to find plants containing both transgenes (¾×¾= ⁹⁄₁₆) and these plants are allowed to self-pollinate. $\frac{1}{9}^{th}$ of these ($\frac{1}{16}^{th}$ of original planting prior to spraying) F1S2S3 seeds from these F1S2 plants will be homozygous for both transgenes and produce homozygous progeny (100% resistant to both chlorsulfuron and cyanamide). Single plant analysis of these F1S2S3 plants can be performed. These are homozygous for both the donor and receptor vectors and can be more extensively studied in this generation. Alternatively, the seeds from the F1S2S2 plants can be bulked up for detailed studies.

Plants are screened for desired plant phenotypes for each gene. Initially studies may be preformed using two component systems where transcription factor expression is activated with the CaMV 35S activator gene. Transcription factors which appear to play a role in interesting phenotypes can then be further investigated by crossing specific receptor vectors with tissue-specific or inducible activator lines, such as fruit specific activator lines, or environmental or disease-inducible lines or developmental-stage specific lines.

Particular traits of interest in tomato include increased levels of carotenoids (particularly lycopene), increased levels of soluble solids, and enhanced disease resistance.

All references (publications and patents) are incorporated herein by reference in their entirety for all purposes.

Although the invention has been described with reference to the embodiments and examples above, it should be understood that various modifications can be made without departing from the spirit of the invention. Accordingly, the invention is limited only by the following claims.

We claim:

1. A method for screening for overexpression of a transcription factor polynucleotide in plants, said method comprising:
   (a) providing a first pool of donor vectors, wherein each donor vector member comprises a LexA DNA binding domain fused to a GAL4 transcription activation domain, and a second pool of receptor vectors, wherein each receptor vector member comprises a LexA DNA binding site operably linked to a transcription factor polynucleotide;
   (b) transforming a first plant with a member of said donor vector pool;
   (c) transforming a second plant with a member of said receptor vector pool;
   (d) crossing said first and second transformed plants to generate a hybrid plant, wherein the hybrid plant comprises the member of said donor vector pool and the member of said receptor vector pool; and
   (e) characterizing the phenotype of said hybrid plant so as to identify a hybrid plant overexpressing the transcription factor polynucleotide.

2. The method of claim 1, wherein said LexA DNA binding domain fused to a GAL4 transcription activation domain is operably linked to a constitutive promoter, an inducible promoter, a tissue-specific promoter, or a developmental-stage specific promoter.

3. The method of claim 1, wherein steps (b) through (e) are performed more than once.

4. The method of claim 1, wherein said first plant is transformed with more than one donor vector member.

5. The method of claim 1, wherein said second plant is transformed with more than one member of said receptor vector pool.

6. The method of claim 1, wherein said donor vector further comprises a selectable marker.

7. The method of claim 1, wherein said receptor vector further comprises a selectable marker.

8. A method for breeding a plant with enhanced tolerance to environmental stress, said method comprising the steps of:
   (a) providing a first transformed plant, wherein said first transformed plant is transformed with a donor vector comprising a LexA DNA binding domain fused to a GAL4 transcription activation domain;
   (b) providing a second transformed plant, wherein said second transformed plant is transformed with a receptor vector comprising a LexA DNA binding site operably linked to a polynucleotide encoding a transcription factor that confers enhanced tolerance to environmental stress when overexpressed;
   (c) crossing said first and second transformed plants to generate a hybrid plant, wherein the hybrid plant comprises the donor vector and the receptor vector; and
   (d) selecting a hybrid plant that overexpresses the transcription factor, wherein the selected hybrid plant has enhanced tolerance to environmental stress.

9. The method of claim 8, wherein said LexA DNA binding domain fused to a GAL4 transcription activation domain is operably linked to a constitutive promoter, an inducible promoter, a tissue-specific promoter, or a developmental-stage specific promoter.

10. The method of claim 8, wherein steps (a) through (d) are performed more then once.

11. The method of claim 8, wherein said first plant is transformed with more than one donor vector.

12. The method of claim 8, wherein said second plant is transformed with more than one receptor vector.

13. The method of claim 8, wherein said donor vector further comprises a selectable marker.

14. The method of claim 8, wherein said receptor vector further comprises a selectable marker.

15. A hybrid plant with enhanced tolerance to environmental stress produced according to the method of claim 8.

16. A method for increasing expression of a transcription factor polynucleotide in a plant, said method comprising:
   (a) providing a first pool of donor vectors, wherein each donor vector member comprises a LexA DNA binding domain fused to a GAL4 transcription activation domain, and a second pool of receptor vectors, wherein each receptor vector member comprises a LexA DNA binding site operably linked to a transcription factor polynucleotide;
   (b) transforming a first plant with a member of said donor pool;
   (c) transforming a second plant with a member of said receptor pool; and
   (d) crossing first and second transformed plants to generate a hybrid plant with increased expression of a transcription factor polynucleotide.

17. The method of claim 16, wherein said LexA DNA binding domain fused to a GAL4 transcription activation domain is operably linked to a constitutive promoter, an inducible promoter, a tissue-specific promoter, or a developmental-stage specific promoter.

18. The method of claim 16, wherein steps (a) through (d) are performed more than once.

19. The method of claim 16, wherein said first plant is transformed with more then one donor vector.

20. The method of claim 16, wherein said second plant is transformed with more than one member of said receptor pool.

21. The method of claim 16, wherein said donor vector further comprises a selectable marker.

22. The method of claim 16, wherein said receptor vector further comprises a selectable marker.

* * * * *

UNITED STATES PATENT AND TRADEMARK OFFICE
CERTIFICATE OF CORRECTION

PATENT NO. : 6,946,586 B1
DATED : September 20, 2005
INVENTOR(S) : Fromm, Michael and Zhang, James It is certified that error appears in the above-identified patent and that said Letters Patent is hereby corrected as shown below:

Column 4,
Line 66, "Identity" should read -- identity --.

Column 7,
Line 11, "wun1" should read -- wunI --.

Column 8,
Line 46, "CATT" should read -- CAAT --.

Column 13,
Line 13, "TCCTCTATATAAGGAAGTTC A" should read
-- TCCTCTATATAAGGAAGTTCA --.
Line 25, "GAATTCCCCAATTAATCAAAGTGGGAA" should read
-- GAATTCCCCAATTTTAATCAAAGTGGGAA --.

Column 14,
Line 47, "TGCATTACAGTTGGGAAAGT" should read
-- TGCATTACAGTTGGGAAGT --.

Column 16,
Line 27, "Itp1" should read -- ltp1 --.

Signed and Sealed this

Third Day of January, 2006

JON W. DUDAS
*Director of the United States Patent and Trademark Office*

SEQUENCE LISTING

<160> NUMBER OF SEQ ID NOS: 21

<210> SEQ ID NO 1
<211> LENGTH: 55
<212> TYPE: DNA
<213> ORGANISM: Artificial Sequence
<220> FEATURE:
<223> OTHER INFORMATION: primer 011731

<400> SEQUENCE: 1
gcccaagctt tgagctccgc ggccgcaaga cccttcctct atataaggaa gttca            55

<210> SEQ ID NO 2
<211> LENGTH: 39
<212> TYPE: DNA
<213> ORGANISM: Artificial Sequence
<220> FEATURE:
<223> OTHER INFORMATION: primer 011733

<400> SEQUENCE: 2
acgcttccat ggtaattgta aatgtaattg taatgttgt            39

<210> SEQ ID NO 3
<211> LENGTH: 40
<212> TYPE: DNA
<213> ORGANISM: Artificial Sequence
<220> FEATURE:
<223> OTHER INFORMATION: primer 011732

<400> SEQUENCE: 3
ttacaattac catggaagcg ttaacggcca ggcaacaaga            40

<210> SEQ ID NO 4
<211> LENGTH: 45
<212> TYPE: DNA
<213> ORGANISM: Artificial Sequence
<220> FEATURE:
<223> OTHER INFORMATION: primer 011717

<400> SEQUENCE: 4
tattcccact ttgattaaaa ttggggaatt ccagccagtc gccgt            45

<210> SEQ ID NO 5
<211> LENGTH: 34
<212> TYPE: DNA
<213> ORGANISM: Artificial Sequence
<220> FEATURE:
<223> OTHER INFORMATION: primer 011715

<400> SEQUENCE: 5
ggctggaatt ccccaatttt aatcaaagtg ggaa            34

```
<210> SEQ ID NO 6
<211> LENGTH: 36
<212> TYPE: DNA
<213> ORGANISM: Artificial Sequence
<220> FEATURE:
<223> OTHER INFORMATION: primer 011718

<400> SEQUENCE: 6
aagctctagc tactcttttt ttgggtttgg tggggt                          36

<210> SEQ ID NO 7
<211> LENGTH: 29
<212> TYPE: DNA
<213> ORGANISM: Artificial Sequence
<220> FEATURE:
<223> OTHER INFORMATION: primer 011716

<400> SEQUENCE: 7
aagagtagct agagctttcg ttcgtatca                                  29

<210> SEQ ID NO 8
<211> LENGTH: 29
<212> TYPE: DNA
<213> ORGANISM: Artificial Sequence
<220> FEATURE:
<223> OTHER INFORMATION: primer 011719

<400> SEQUENCE: 8
tgctctagat tgatgcatgt tgtcaatca                                  29

<210> SEQ ID NO 9
<211> LENGTH: 73
<212> TYPE: DNA
<213> ORGANISM: Artificial Sequence
<220> FEATURE:
<223> OTHER INFORMATION: primer 016400

<400> SEQUENCE: 9
catgccatgg aaccagtaac gttatacgat gtcgcagagt atgccggtgt ctctcatcag    60
accgtttccc gcg                                                   73

<210> SEQ ID NO 10
<211> LENGTH: 36
<212> TYPE: DNA
<213> ORGANISM: Artificial Sequence
<220> FEATURE:
<223> OTHER INFORMATION: primer 016401

<400> SEQUENCE: 10
ggggaattca aggtggttt ttcttttcac cagtga                           36

<210> SEQ ID NO 11
<211> LENGTH: 31
<212> TYPE: DNA
<213> ORGANISM: Artificial Sequence
<220> FEATURE:
<223> OTHER INFORMATION: rd29a-primer1

<400> SEQUENCE: 11
gcccaagctt ggttgctatg gtagggacta t                               31

<210> SEQ ID NO 12
<211> LENGTH: 42
<212> TYPE: DNA
```

-continued

```
<213> ORGANISM: Artificial Sequence
<220> FEATURE:
<223> OTHER INFORMATION: rd29a-primer2

<400> SEQUENCE: 12
ataagaatgc ggccgcgaga gataaaggga cacgtatgaa gc                          42

<210> SEQ ID NO 13
<211> LENGTH: 37
<212> TYPE: DNA
<213> ORGANISM: Artificial Sequence
<220> FEATURE:
<223> OTHER INFORMATION: LTP1-primer1

<400> SEQUENCE: 13
gcccaagctt gattaacttg cattacagtt gggaagt                                37

<210> SEQ ID NO 14
<211> LENGTH: 44
<212> TYPE: DNA
<213> ORGANISM: Artificial Sequence
<220> FEATURE:
<223> OTHER INFORMATION: LTP1-primer2

<400> SEQUENCE: 14
ataagaatgc ggccgcggta cgtatatgtt atgtggtgtg aatg                        44

<210> SEQ ID NO 15
<211> LENGTH: 35
<212> TYPE: DNA
<213> ORGANISM: Artificial Sequence
<220> FEATURE:
<223> OTHER INFORMATION: primer 016417

<400> SEQUENCE: 15
ggcccaagct tacatatcca tatctaatct tacct                                  35

<210> SEQ ID NO 16
<211> LENGTH: 28
<212> TYPE: DNA
<213> ORGANISM: Artificial Sequence
<220> FEATURE:
<223> OTHER INFORMATION: primer 016416

<400> SEQUENCE: 16
ctagaggatc cggtacgagg cctgtcta                                          28

<210> SEQ ID NO 17
<211> LENGTH: 55
<212> TYPE: DNA
<213> ORGANISM: Artificial Sequence
<220> FEATURE:
<223> OTHER INFORMATION: primer 016415

<400> SEQUENCE: 17
ggcccaagct taattgtgag cgctcacaat tcatgaattg tgagcgctca caatt            55

<210> SEQ ID NO 18
<211> LENGTH: 35
<212> TYPE: DNA
<213> ORGANISM: Artificial Sequence
<220> FEATURE:
<223> OTHER INFORMATION: primer 011700

<400> SEQUENCE: 18
acgcgtcgac gactgagaac tctagtaact acgta                                  35
```

```
<210> SEQ ID NO 19
<211> LENGTH: 41
<212> TYPE: DNA
<213> ORGANISM: Artificial Sequence
<220> FEATURE:
<223> OTHER INFORMATION: primer 011702

<400> SEQUENCE: 19
ataagaatgc ggccgccgac tatcgaatat tagtaactcc a                     41

<210> SEQ ID NO 20
<211> LENGTH: 34
<212> TYPE: DNA
<213> ORGANISM: Artificial Sequence
<220> FEATURE:
<223> OTHER INFORMATION: primer 05184

<400> SEQUENCE: 20
cggggtaccc ttctccacaa gtaagggaac caga                             34

<210> SEQ ID NO 21
<211> LENGTH: 43
<212> TYPE: DNA
<213> ORGANISM: Artificial Sequence
<220> FEATURE:
<223> OTHER INFORMATION: primer 05185

<400> SEQUENCE: 21
ataagaatgc ggccgccctc ccctttcact cttaccttcc gaa                   43
```